United States Patent

Shum et al.

Patent Number: 5,663,384
Date of Patent: Sep. 2, 1997

[54] ASYMETRIC EPOXIDATION USING A TITANIUM-CONTAINING ZEOLITE AND A CHIRAL HYDROPEROXIDE

[75] Inventors: Wilfred Po-sum Shum; Robert J. Saxton, both of West Chester; John G. Zajacek, Devon, all of Pa.

[73] Assignee: ARCO Chemical Technology, L.P., Greenville, Del.

[21] Appl. No.: 611,732

[22] Filed: Mar. 6, 1996

[51] Int. Cl.$^6$ .................................................. C07D 301/19
[52] U.S. Cl. ......................................................... 549/529
[58] Field of Search ............................................ 549/529

[56] References Cited

U.S. PATENT DOCUMENTS

| | | | |
|---|---|---|---|
| 4,471,130 | 9/1984 | Katsuyi et al. | 549/523 |
| 4,764,628 | 8/1988 | Shum | 549/529 |
| 4,900,847 | 2/1990 | Hanson et al. | 549/529 |
| 4,946,973 | 8/1990 | Frank | 549/529 |
| 5,166,371 | 11/1992 | Shum et al. | 549/529 |
| 5,354,875 | 10/1994 | Nemeth et al. | 549/529 |
| 5,374,747 | 12/1994 | Saxton et al. | 549/531 |
| 5,453,511 | 9/1995 | Saxton | 546/191 |
| 5,466,835 | 11/1995 | Nemeth et al. | 549/529 |

FOREIGN PATENT DOCUMENTS

| | | |
|---|---|---|
| 0070618 | 1/1983 | European Pat. Off. . |
| 2037596 | 6/1993 | Spain . |
| 9402245 | 2/1994 | WIPO . |

*Primary Examiner*—Bernard Dentz
*Assistant Examiner*—Lyman H. Smith
*Attorney, Agent, or Firm*—Stephen D. Harper

[57] ABSTRACT

Prochiral ethylenically unsaturated substrates are converted to chiral epoxides by reaction with optically active hydroperoxides in the presence of titanium-containing zeolites such as titanium zeolite beta. The method is particularly suitable for producing epoxides from unsubstituted aliphatic olefins which have exceptionally high optical purity as measured by enantiomeric excess.

17 Claims, No Drawings

ASYMETRIC EPOXIDATION USING A TITANIUM-CONTAINING ZEOLITE AND A CHIRAL HYDROPEROXIDE

FIELD OF THE INVENTION

The present invention is related to the asymmetric epoxidation of prochiral ethylenicailly unsaturated substrates. The epoxides obtained by the process of this invention are optically active and are useful as synthetic intermediates in the preparation of pharmaceuticals, liquid crystal polymers, and the like.

BACKGROUND OF THE INVENTION

Methods have been developed which are capable of epoxidizing functionalized olefins such as allylic alcohols to form epoxides having a high degree of optical purity. For example, U.S. Pat. Nos. 4,471,130 and 4,764,628 teach the epoxidation of allylic alcohols using racemic or non-chiral organic hydroperoxides and soluble titanium complexes containing optically active alkoxide substituents as catalysts. More recently, the use of chiral hydroperoxides in combination with certain transition metal catalysts has been proposed (U.S. Pat. No. 5,166,371). Unfortunately, such methods are apparently not capable of providing epoxide products in high enantiomeric excess where the initial unsaturated substrate is unfunctionalized (i.e., does not contain an active hydrogen functional group such as hydroxyl).

It thus would be highly desirable to develop alternative synthetic methods by which unfunctionalized substrates may be epoxidized in an asymmetric manner to yield optically active products having a satisfactorily high degree of optical purity.

SUMMARY OF THE INVENTION

The invention is a method for producing an optically active epoxide which comprises reacting a prochiral ethylenically unsaturated substrate with an optically active hydroperoxide in the presence of a titanium-containing zeolite.

In a particularly preferred embodiment, the invention comprises reacting a prochiral $C_3$–$C_{10}$ aliphatic olefin with an optically active hydroperoxide having an optical purity as measured by enantiomeric excess of at least 10% and the general structure

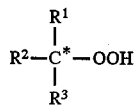

wherein $R^1$, $R^2$, and $R^3$ are different and $R^1$ is hydrogen or methyl, $R^2$ is methyl or ethyl, and $R^3$ is phenyl, naphthyl, or propyl, in the presence of a titanium-containing zeolite having a zeolite beta topology and the composition $xTiO_2$:$(1-x)$ $SiO_2$ where x is from 0.01 to 0.125 at a temperature of from $-30°$ C. to $50°$ C.

DETAILED DESCRIPTION OF THE INVENTION

Any suitable prochiral ethylenically unsaturated substrate may be asymmetrically epoxidized in accordance with the process of this invention. The term "prochiral" indicates that the substrate structure must make possible the formation of optically active epoxidized product. Symmetrically substituted ethylenically unsaturated substrates such as ethylene and tetramethylethylene thus are not suitable for use as substrates in this process since the corresponding epoxides will be achiral. The substrate must be capable of accessing the interior cavities of the titanium-containing zeolite which is selected for use. That is, the molecular dimensions of the substrate should be such that the substrate is able to diffuse into the zeolite pores.

Examples of suitable ethylenically unsaturated substrates include, for example, substituted and unsubstituted aliphatic, alicyclic, and aromatic olefins which may be hydrocarbons, esters, alcohols, ketones, ethers, halides, or the like. The substrate may contain more than one carbon-carbon double bond and may be monomeric, oligomeric, or polymeric in nature. One class of preferred substrates comprises aliphatic and aromatic olefins having from 3 to 30 carbon atoms. Illustrative olefins are terminal or internal olefins such as propylene, 1-butene, 1-pentene, 2-pentene, 1-hexene, 2-hexene, 1-heptene, 2-heptene, 3-heptene, 1-octene, 2-octene, and 3-octene, aromatic vinyl compounds such as styrene and substituted styrenes, branched olefins such as 2-methyl-1-pentene and neohexene, and substituted cycloolefins such as 3-methyl-1-cyclohexene. Ethylenically unsaturated substrates having substituents containing halogen, oxygen, sulfur, or the like can be used, including, for example, allyl chloride, methallyl chloride, methyl methacrylate, methyl vinyl ketone, and the like.

The process of this invention is particularly advantageous for use with olefins characterized by the absence of hydroxyl groups, especially $C_3$–$C_{10}$ aliphatic olefins.

Any optically active hydroperoxide may be used in the process of this invention provided it possesses at least one chiral center. Preferably, the hydroperoxide is organic with the chiral center being the carbon bearing the hydroperoxy functionality. Hydroperoxides of this type thus can be secondary or tertiary and will have four different substituents attached to the hydroperoxy carbon. In one embodiment, the three substituents directly attached to the hydroperoxy carbon other than the oxygen of the hydroperoxy group are hydrogen or hydrocarbon substituents. In other embodiments, however, one or more of the substituents may be functionalized with, for example, a ketone or hydroxy group. Although generally it will be advantageous to employ a single optically active hydroperoxide, mixtures of different optically active hydroperoxides may also be used. The optically active hydroperoxide may contain more than one hydroperoxy group. Since the degree of stereoselectivity during epoxidation is to some extent dependent on the optical purity of the hydroperoxide reagent, it is preferred to employ hydroperoxide in which one stereoisomer greatly predominates. In general, the hydroperoxide should have an optical purity (as measured by enantiomeric excess) of at least about 10%. More preferably, the optical purity is at least about 50%. Most preferably, the enantiomeric excess of the optically active hydroperoxide is at least about 75%.

In certain embodiments, the optically active hydroperoxides include those compounds corresponding to the general structure:

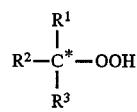

wherein $R^1$, $R^2$, and $R^3$ are different and are radicals selected from the group consisting of hydrogen, $C_1$–$C_{12}$ linear, branched, or cyclic alkyl, aralkyl, substituted aralkyl, aryl, or substituted aryl. In this structure, "*" indicates a chiral center. Illustrative radicals include methyl, ethyl, propyl, isopropyl, butyl, sec-butyl, iso-butyl, t-butyl, $C_5$–$C_{12}$ linear and branched aliphatic radicals, cyclohexyl, methyl cyclohexyl, cyclopentyl, benzyl, phenethyl, tolyl, naphthyl, phenyl, halophenyl, and the like. The radicals may contain elements other than carbon and hydrogen such as oxygen, halogen, and sulfur, provided these other elements or functional groups do not interfere with the desired asymmetric epoxidation. Particularly preferred optically active hydroperoxides are those where $R^1$ is hydrogen or methyl, $R^2$ is methyl or ethyl, and $R^3$ is phenyl, naphthyl, or propyl, provided each R group is different. Illustrative examples of such hydroperoxides include ethyl benzene hydroperoxide ($R^1$=H, $R^2$=methyl, $R^3$=phenyl), ethyl naphthalene hydroperoxide ($R^1$=H, $R^2$=methyl, $R^3$=naphthyl), propyl benzene hydroperoxide ($R^1$=H, $R^2$=ethyl, $R^3$=phenyl), 2-hydroperoxy pentane ($R^1$=H, $R^2$=methyl, $R^3$=propyl), 2-hydroperoxy-2-phenyl butane ($R^1$=methyl, $R^2$=ethyl, $R^3$=phenyl), 3-hydroperoxy-3-methyl hexane ($R^1$=methyl, $R^2$=ethyl, $R^3$=propyl), and 2-hydroperoxy butane ($R^1$=methyl, $R^2$=hydrogen, $R^3$=ethyl). Optically active ethylbenzene hydroperoxide, which may be prepared in racemic form by oxidation of ethylbenzene and subsequently resolved using any of the methods known in the art, is the preferred hydroperoxide because of its relatively low cost and availability.

Hydroxyhydroperoxides represent another class of optically active hydroperoxides suitable for use in the process of the invention. Such substances contain a hydroxy group in addition to the hydroperoxy group, most preferably on one of the carbon atoms alpha to the carbon atom bearing the hydroperoxy group. Hydroxyhydroperoxides may be obtained by ring-opening of a chiral epoxide such as (R)- or (S)-propylene oxide with hydrogen peroxide. Reaction of an optically active hydroxyhydroperoxide of this type with a prochiral olefin under the conditions of the present invention yields two synthetically useful products in optically active form: the epoxide of the olefin and also the glycol corresponding to the hydroperoxide.

Optically active hydroperoxides bearing ketone groups are also useful in the asymmetric epoxidation process described herein, particularly those where the ketone is alpha to the carbon bearing the hydroperoxide group such as, for example:

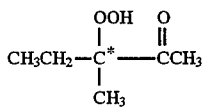

Any suitable method may be used to obtain the optically active hydroperoxide. A number of such methods have been described in the art, including enzymatic resolution of racemic hydroperoxides [N. Baba, et al. *Agric. Biol. Chem.* 52, 2685 (1988), Adam et al., *J. Am. Chem. Soc.* 11898 (1995), and Hoft et al., *Tetrahedron-Asymmetry* 6,603 (1995)], singlet oxygenation of thiazolidine derivatives [T. Takata, et al. *Bull. Chem. Soc. Jpn.* 59, 1275 (1986)], perhydrolysis of optically active ketals, Schiff's bases or isoindolones [J. Rebek, Jr., et al. *J. Am. Chem. Soc.* 102, 5602 (1980)], liquid chromatographic resolution and subsequent hydrolysis of perketals [P. Dussault, et al. *J. Am. chem. Soc.* 110, 6276 (1988)], oxidation of optically active 1-phenylethanol [A. G. Davies, et al. *J. A. Chem. Soc* 665 (1956); *J. Chem. Soc* (B), 17 (1967)], oxidation of optically active halides with platinum dioxygen complexes [Y. Tatsuno et al *J.A. Chem. Soc.* 103, 5832 (1981)], kinetic resolution of hydroperoxide using Sharpless epoxidation [Hoft et al., *Tetrahedron-Asymmetry* 3, 507 (1992)], and reaction of chiral secondary alkyl methane sulfonates with alkaline hydrogen peroxide [Williams et al., *J. Am. Chem. Soc.* 76, 2987 (1954)].

The titanium-containing zeolites suitable for use as the catalyst in the present process comprise the class of crystalline zeolitic substances wherein titanium is substituted for a portion of the silicon or aluminum atoms in the lattice framework of a silicate or aluminosilicate molecular sieve. Titanium-containing zeolites are characterized by their insolubility in organic media. Such substances are well-known in the art.

When the optically active hydroperoxide is (R)- or (S)-ethyl benzene hydroperoxide, titanium-containing molecular sieves having framework structures isomorphous to zeolite beta (a zeolite with intersecting 12-membered rings measuring 6.5×5.6 and 7.5×5.7 angstroms) are especially preferred for use. Such zeolites are described in U.S. Pat. Nos. 5,474,754 and 5,453,511, Camblor et al., *Heterogeneous Catalysis and Fine Chemicals III*, 393–399 (1993), PCT Publication No. WO 94/02245, French Pat. Doc. No. 2,694,549, and U.S. Pat. Nos. 4,892,720, 5,098,687, 5,233,097, and 5,271,761. The titanium-containing zeolite preferably contains no atoms other than oxygen, titanium and silica in the lattice framework, although minor amounts of boron, iron, aluminum, phosphorus and the like may be present. The zeolite preferably is essentially free of aluminum (i.e., less than 1000 ppm Al is present), as higher selectivity to epoxide is generally obtained with such catalysts.

Without wishing to be bound by theory, it is thought that the high enantioselectivity possible by practice of this invention is a result of the constrained geometry of the hydroperoxide within the confines of the zeolite cavity. For example, the physical dimensions of both (S)-ethyl benzene hydroperoxide and a titanium-containing zeolite having a beta topology encourage oxygen transfer only from one face of the hydroperoxide to the ethylenically unsaturated substrate. Inversion of the hydroperoxide is discouraged due to stearic hinderance. It is believed that by selecting an organic hydroperoxide of appropriate dimensions, any zeolite framework morphology which contains titanium in its framework could be used in the present process to catalyze the desired epoxidation with a satisfactorily high degree of enantioselectivity. Put a different way, the titanium-containing molecular sieve should be selected to have pore, channel, and cavity dimensions which are sufficiently large to allow the hydroperoxide and substrate to diffuse into the zeolite to reach the catalytically active titanium sites, yet not so large that said molecules are unconstrained to the degree necessary to accomplish asymmetric epoxidation.

Accordingly, when hydroperoxides which are more linear and/or less bulky than ethyl benzene hydroperoxide are utilized (e.g., 2-hydroperoxy butane), it is expected that a medium pore zeolite such as TS-1 or TS-2 titanium silicalite (titanium-containing zeolites having respectively MFI and MEL structures) or Ti-ZSM-48 may provide a higher degree of enantioselectivity than large pore zeolites such as those having a beta, ZSM-12, Ti-mordenite or ETS-10 structure. Similarly, if a hydroperoxide substantially larger than ethyl benzene hydroperoxide is employed, the use of an ultra large pore titanium-containing zeolite (i.e., a zeolite having pore dimensions larger than beta) such as Ti-MCM-41 or Ti-HMS-1 may be desirable.

Epoxidation catalysts suitable for use in the process of this invention will typically have a composition corresponding to the following empirical formula $xTiO_2$:$(1-x)SiO_2$, wherein x is preferably from 0.01 to 0.125. The molar ratio of Si:Ti in the lattice framework of the titanium-containing zeolite is advantageously from 9.5:1 to 99:1 (most preferably, from 9.5:1 to 60:1).

The amount of catalyst employed is not critical, but should be sufficient so as to substantially accomplish the desired epoxidation reaction in a practicably short period of time. The optimum quantity of catalyst will depend upon a number of factors including reaction temperature, substrate reactivity and concentration, hydroperoxide concentration, type and concentration of organic solvent as well as catalyst activity and the type of reactor or reaction system employed. In a batch-type or slurry reaction, for example, the amount of catalyst will typically be from 0.0001 to 10 grams per mole of substrate. In a fixed bed system, the optimum quantity of catalyst will be influenced by the flow rate of reactants through the fixed bed (typically, from about 0.05 to 2.0 kilograms hydroperoxide per kilogram catalyst per hour). The concentration of titanium in the total epoxidation reaction mixture will generally be from about 10 to 10,000 ppm.

The catalyst may be utilized in powder, pellet, microspheric, extruded, monolithic or any other suitable physical form. The use of a binder (co-gel) or support in combination with the titanium-containing zeolite may be advantageous. Supported or bound catalysts may be prepared by the methods known in the art to be effective for zeolite catalysts in general. Preferably, the binder or support is essentially non-acidic and does not catalyze the non-selective decomposition of the hydroperoxide or ring-opening or racemization of the epoxide product.

The process of this invention is preferably carried out in a liquid medium, preferably an inert organic solvent in which all of the reaction components (other than the catalyst) are soluble. Preferred organic solvents include halogenated hydrocarbons such as methylene chloride and carbon tetrachloride, aromatic hydrocarbons such as toluene, ethyl benzene and benzene, and aliphatic hydrocarbons such as heptane and isooctane. It is preferred that the reaction medium be anhydrous; the use of a desiccant such as molecular sieves can be advantageous. Although not critical, the asymmetric epoxidation is preferably carried out under an inert atmospheric (nitrogen or argon, for example).

The reaction temperature and time required will vary from about 1 minute to 7 days at from about −100° C. to 150° C., depending on the catalyst, ethylenically unsaturated substrate, and optically active hydroperoxide used. Where the titanium-containing zeolite has a large pore topology such as zeolite beta, the substrate is a $C_3$–$C_{10}$ aliphatic olefin, and the hydroperoxide is ethyl benzene hydroperoxide, for example, it is particularly preferred to carry out the reaction in the temperature range of from −30° C. to 50° C., as the optical purity (% e.e.) of the epoxide product is generally satisfactorily high in said range. Typical reaction times under such conditions are from as little as 1 hour up to 30 hours. The time is not critical and can readily be optimized for a particular set of conditions and reactants. In any event, the reaction time and temperature should be selected so as to accomplish effective stereoselective epoxidation of the ethylenically unsaturated substrate (i.e., a chiral induction of at least 20%, more preferably at least 40%, most preferably at least 60%)

The manner in which the reactants are combined is not critical, but generally slow addition of the optically active hydroperoxide to a mixture of catalyst, ethylenically unsaturated substrate, and, optionally, solvent will be preferred.

The molar ratio of hydroperoxide to substrate is not critical and may vary widely (e.g., from 50:1 to 1:50). For reasons of economy, the molar ratio of hydroperoxide to substrate is preferably not greater than about 3:1.

After epoxidation has been completed to the desired degree, the optically active epoxide may be separated from the reaction medium by any suitable means. Such methods will be apparent to those skilled in the art and generally will be analogous to the procedures employed for the recovery of epoxides prepared by other epoxidation processes. Where the epoxide product is water-insoluble and relatively volatile, recovery can be effected by fractional distillation. Epoxide products which are crystalline solids at room temperature may be purified by recrystallization from an appropriate solvent. If the optically active epoxide is water-soluble, salting out, extraction or chromatography may be used. Prior to any purification step involving heating of the product significantly above the epoxidation reaction temperature, it is highly desirable to first separate the titanium-containing molecular sieve (by filtration or other such means) and to reduce any remaining unreacted hydroperoxide. Alternatively, the optically active epoxide is not isolated but reacted in situ to form useful derivatives such as substituted benzene sulfonates, trityl ethers, ring-opened products (by reaction with amines or alcohols, for example) and the like.

Without further elaboration, it is believed that one skilled in the art can, using the preceding description, utilize the present invention to its fullest extent. The following examples, therefore, are to be considered as merely illustrative and not limitative of the claims or remainder of the disclosure in any way whatsoever.

EXAMPLES

Percent chiral induction in the following examples was calculated using the following formula:

$$\frac{\% \text{ e.e. of epoxide produced}}{\% \text{ e.e. of chiral hydroperoxide}} \times 100$$

In a typical experimental procedure, a mixture containing 1.4 mL ethyl benzene, 6 mmol of ethylenically unsaturated substrate, 0.75 mmol optically active (S)-ethylbenzene hydroperoxide (as a 35 wt % solution in ethyl benzene) is stirred at −15° C. for 10 hours to obtain an enantiomerically enriched epoxide product. The product is analyzed by a chiral gas chromatography method using a capillary cyclodextrin-based column supplied by Advanced Separation Technologies.

Example 1

Epoxidation of 1-hexene was performed at −15° C. using a titanium-containing zeolite having a beta topology (prepared in accordance with the hydrothermal synthesis method described in U.S. Pat. No. 5,453,511) with 98% ee (S)-ethyl benzene hydroperoxide (35 wt % in ethyl benzene; prepared in accordance with the lipase-catalyzed kinetic resolution method described in Baba et al., Agric. Biol. Chem. 52, 2685 (1988)) to obtain (R)-1,2-epoxy hexane in 63% e.e. The % chiral induction was 64%.

Example 2

Epoxidation of 1-hexene was performed at −15° C. using 59% e.e. (S)-ethylbenzene hydroperoxide and the zeolite of Example 1 to obtain (R)-1,2-epoxy hexane in 34% e.e. The % chiral induction was 64%.

Example 3

To demonstrate the effect of reaction temperature on chiral induction, epoxidation of 1-hexene was carried out at ambient temperature (ca. 20° C.) using 98% e.e. (S)-ethyl benzene hydroperoxide and the zeolite of Example 1. The e.e. value of the (R)-1,2-epoxy hexane obtained was only 3%. The % chiral induction was 3%.

Example 4 (Control)

To demonstrate that the epoxide product enriched in one enantiomer is not the result of kinetic resolution, racemic 1,2-epoxyhexane was combined with the zeolite of Example 1 and (S)-ethyl benzene hydroperoxide (spiked with (s)-sec-phenethyl alcohol) and stirred at −10° C. overnight. Analysis by gas chromatography indicated that no enantiomeric enrichment of the epoxide took place.

Example 5 (Comparative)

To demonstrate the criticality of using a titanium-containing zeolite as a catalyst rather than another type of heterogeneous titanium material, epoxidation of 1-hexene was performed at −15° C. using 98% e.e. (S) ethyl benzene hydroperoxide and a non-zeolitic titania-on-silica catalyst prepared in accordance with the procedures described in U.S. Pat. No. 3,923,843. Racemic 1,2-epoxy hexane was obtained.

Example 6

Epoxidation of 1-hexene was attempted at −15° C. using 59% e.e. (S)-ethylbenzene hydroperoxide and the ultra large pore silicotitanate zeolite described in European Pat. Publ. No. 655,278 (having a crystalline structure similar to MCM-41 zeolite). Racemic 1,2-epoxyhexane was produced in very low yield. A titanium-containing zeolite of this type is expected to be better suited for asymmetric epoxidation using optically active hydroperoxides larger in size than ethyl benzene hydroperoxide and/or ethylenically unsaturated substrates larger in size than 1-hexene.

Example 7

To demonstrate that the process of the invention is suitable for the asymmetric epoxidation of internal olefins, cis-2-pentene was reacted at −20° C. with 98% e.e. (S)-ethyl benzene hydroperoxide and the zeolite of Example 1. The enantiopurity of the cis-2,3-epoxide produced was 54% e.e. Chiral induction was 55%.

Example 8

The procedure of Example 7 was repeated, except that the reaction was carried out at 0° C. The enantiopurity of the cis-2,3-epoxide decreased to 20% e.e. (chiral induction= 20%).

We claim:

1. A method for producing an optically active epoxide which comprises reacting a prochiral ethylenically unsaturated substrate characterized by the absence of hydroxyl groups with an optically active hydroperoxide in the presence of a titanium-containing zeolite.

2. The method of claim 1 wherein the prochiral ethylenically unsaturated substrate is a $C_3$–$C_{10}$ aliphatic olefin.

3. The method of claim 1 wherein the optically active hydroperoxide has the general structure

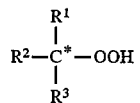

wherein $R^1$, $R^2$, and $R^3$ are different and are selected from the group consisting of hydrogen, $C_1$–$C_{12}$ linear, branched, or cyclic alkyl, aralkyl, substituted aralkyl, aryl and substituted aryl.

4. The method of claim 1 wherein the optically active hydroperoxide is ethylbenzene hydroperoxide.

5. The method of claim 1 wherein the optically active hydroperoxide has an optical purity as measured by enantiomeric excess of at least 10%.

6. The method of claim 1 wherein said reacting is performed in an inert organic solvent.

7. The method of claim 1 wherein the titanium-containing zeolite has a zeolite beta topology.

8. The method of claim 1 wherein the titanium-containing zeolite has a zeolite beta topology and is essentially free of aluminum.

9. The method of claim 1 wherein the titanium-containing zeolite has the composition $xTiO_2:(1-x)SiO_2$ where x is from 0.01 to 0.125.

10. The method of claim 1 wherein said reacting is performed at a temperature of from −30° C. to 50° C.

11. The method of claim 1 wherein the titanium-containing zeolite is a large pore titanium-containing zeolite.

12. A method for producing an optically active epoxide which comprises reacting a prochiral $C_3$–$C_{10}$ aliphatic olefin characterized by the absence of hydroxyl groups with an optically active hydroperoxide having an optical purity as measured by enantiomeric excess of at least 10% and the general structure

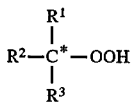

wherein $R^1$, $R^2$, and $R^3$ are different and $R^1$ is hydrogen or methyl, $R^2$ is methyl or ethyl, and $R^3$ is phenyl, naphthyl, or propyl, in the presence of a titanium-containing zeolite having a zeolite beta topology and the composition $xTiO_2:(1-x)SiO_2$ where x is from 0.01 to 0.125 at a temperature of from −30° C. to 50° C.

13. The method of claim 12 wherein said reacting is performed under anhydrous conditions.

14. The method of claim 12 wherein the optically active hydroperoxide is ethyl benzene hydroperoxide.

15. The method of claim 12 wherein the titanium-containing zeolite is essentially free of aluminum.

16. The method of claim 12 wherein the prochiral $C_3$–$C_{10}$ aliphatic olefin is selected from the group consisting of 1-hexene, trans-2-hexene, 1-octene, 3-methyl-1-butene, and cis-2-pentene.

17. The method of claim 12 wherein said reacting is performed in the aresence of an inert organic solvent.

* * * * *

UNITED STATES PATENT AND TRADEMARK OFFICE
CERTIFICATE OF CORRECTION

PATENT NO. : 5,663,384
DATED : Sep. 2, 1997
INVENTOR(S) : Shum et al.

It is certified that error appears in the above-identified patent and that said Letters Patent is hereby corrected as shown below:

On the title page, and col. 1:

<u>Title as filed</u>: delete "ASYMETRIC" and insert therefor --ASYMMETRIC--.

<u>Column 1, line 1</u>: delete "ASYMETRIC" and insert therefor --ASYMMETRIC--.

<u>Column 1, line 6</u>: delete "ethylenicailly" and insert therefor --ethylenically--.

<u>Column 8, line 59</u>: delete "aresence" and insert therefor --presence--.

Signed and Sealed this

Second Day of December,1997

Attest:

BRUCE LEHMAN

Attesting Officer

Commissioner of Patents and Trademarks